(12) United States Patent
Foucault (10) Patent No.: US 10,144,039 B2
(45) Date of Patent: Dec. 4, 2018

(54) METHOD FOR CLEANING TEST SAMPLE WELLS, AND CLEANING HEAD USING SAID METHOD

(71) Applicant: BioMerieux, Marcy l'etoile (FR)

(72) Inventor: Frederic Foucault, Craponne (FR)

(73) Assignee: BIOMERIEUX, Marcy-l'Etoile (FR)

(*) Notice: Subject to any disclaimer, the term of this patent is extended or adjusted under 35 U.S.C. 154(b) by 798 days.

(21) Appl. No.: 14/395,182

(22) PCT Filed: Apr. 17, 2013

(86) PCT No.: PCT/FR2013/050847
§ 371 (c)(1),
(2) Date: Oct. 17, 2014

(87) PCT Pub. No.: WO2013/156736
PCT Pub. Date: Oct. 24, 2013

(65) Prior Publication Data
US 2015/0075565 A1    Mar. 19, 2015

(30) Foreign Application Priority Data

Apr. 19, 2012   (FR) ...................................... 12 53607

(51) Int. Cl.
*B08B 3/04*    (2006.01)
*B01L 3/00*    (2006.01)
*B01L 99/00*   (2010.01)

(52) U.S. Cl.
CPC .............. *B08B 3/04* (2013.01); *B01L 3/5027* (2013.01); *B01L 99/00* (2013.01); *B01L 2300/0636* (2013.01); *B01L 2300/0838* (2013.01)

(58) Field of Classification Search
None
See application file for complete search history.

(56) References Cited

U.S. PATENT DOCUMENTS 3,849,830 A    11/1974  Wagner
3,949,771 A    4/1976   Dodge et al.
(Continued)

FOREIGN PATENT DOCUMENTS

CN    201049348 Y    4/2008
CN    203281537 U    11/2013
(Continued)

OTHER PUBLICATIONS

English Translation of JP2009-222700 to Matsuba, accessed on Jul. 2017.*

(Continued)

*Primary Examiner* — Eric W Golightly
*Assistant Examiner* — Arlyn I Rivera-Cordero
(74) *Attorney, Agent, or Firm* — Ladas & Parry LLP; Malcolm J. MacDonald (57) ABSTRACT

A method for cleaning a test sample well, provided in a diagnostic test card, using a cleaning head having a cleaning tube delivering, at its free end, a cleaning fluid, and a suction tube mounted inside the cleaning tube for aspirating the contaminated cleaning fluid from its free end located in proximity to the free end of the cleaning tube. The method provides for relative displacement between the test card and the cleaning head, so that the test card occupies a cleaning position wherein the cleaning tube delivers, at its free end, the cleaning fluid to the inside of the well to be cleaned and the suction tube aspirates the contaminated cleaning fluid.

9 Claims, 4 Drawing Sheets

(56) References Cited

U.S. PATENT DOCUMENTS

| | | | |
|---|---|---|---|
| 4,227,886 A * | 10/1980 | Bullock | G01N 21/9018 |
| | | | 134/113 |
| 4,559,664 A | 12/1985 | Bohme et al. | |
| 4,635,665 A | 1/1987 | Namba et al. | |
| 5,158,101 A | 10/1992 | Sakka | |
| 5,184,634 A | 2/1993 | Kitajima | |
| 5,636,647 A | 6/1997 | Keene et al. | |
| 5,730,938 A | 3/1998 | Carbonari et al. | |
| 5,882,597 A | 3/1999 | Astle | |
| 2005/0058577 A1 * | 3/2005 | Micklash, II | B01L 3/021 |
| | | | 422/400 |
| 2005/0178795 A1 * | 8/2005 | Inoue | G01N 35/1009 |
| | | | 222/23 |

FOREIGN PATENT DOCUMENTS

| | | |
|---|---|---|
| JP | 55-116239 A | 9/1980 |
| JP | 63-269060 A | 11/1988 |
| JP | 1062431 A | 3/1998 |
| JP | 2009-222700 A | 10/2009 |
| JP | 2009-236838 A | 10/2009 |
| JP | 2010-164421 A | 7/2010 |
| WO | 0058010 A | 10/2000 |

OTHER PUBLICATIONS

International Search Report dated Jun. 20, 2013, corresponding to International Patent Application PCT/FR2013/050847.
Chinese Office Action dated Dec. 3, 2015, corresponding to Chinese Patent Application No. 201310150034.4.
Non-English Japanese Office Action dated Dec. 6, 2016 for Japanese Application No. 2015-506291.
Espacenet English abstract of JP 2009-222700 A, Date:Oct. 2009.
Espacenet English abstract of JP 2010-164421 A, Date:Jul. 2010.
Espacenet English abstract of JP 55-116239 A, Date: Sep. 1980.
Espacenet English abstract of JP 63-269060 A, Date: Nov. 1988.
Espacenet English abstract of JP 2009-236838 A, Date: Oct. 2009.

* cited by examiner

METHOD FOR CLEANING TEST SAMPLE WELLS, AND CLEANING HEAD USING SAID METHOD

This application is a 371 of PCT/FR2013/050847, filed on Apr. 17, 2013, which claims priority to French Application No. 1253607, filed Apr. 19, 2012.

SUMMARY OF THE INVENTION

The present invention relates to the technology of microfluidic systems generally, and it relates more particularly to the field of diagnostic test cards wherein are formed channels for supplying fluid, leading to wells designed to accommodate a reagent and a test or fluid sample containing analytes to be detected, representing an illness or the presence of microorganisms.

BACKGROUND OF THE INVENTION

The object of the invention relates more precisely to technical means suitable for cleaning the wells of such test cards.

The prior art has proposed various devices for cleaning the wells of a test card. For example, U.S. Pat. No. 4,635,665 describes a cleaning device comprising at least one washing head with two coaxial tubes designed to be inserted into the interior of the well to be cleaned to extend in proximity to the bottom of the well. The cleaning head comprises a cleaning tube delivering, at its free end, a cleaning fluid, and a suction tube mounted concentrically within the cleaning tube and designed to aspirate the contaminated cleaning fluid. The adjoining ends of the suction tube and the cleaning tube are situated in one and the same plane to ensure effective aspiration. Injection of the cleaning liquid at the center of the head and the aspiration of the contaminated liquid at the periphery of the head does not make it possible to ensure total recovery of the contaminated liquid.

U.S. Pat. No. 5,882,597 describes a cleaning device comprising a series of cleaning heads each comprising a cleaning tube communicating with a cleaning fluid storage chamber and delivering, at its free end, a cleaning fluid. Each cleaning head also comprises a suction tube for aspirating the contaminated cleaning fluid from its free end, which extends beyond the free end of the cleaning tube. The terminal portion of the cleaning tube is flared to ensure that the liquid leaves in an annular pattern so as to ensure fluid-tightness preventing air from rising into the storage chamber. The cleaning head is displaced so as to enter the interior of the well to be cleaned.

It appears difficult in practice to ensure coaxial mounting of the two tubes, so the proper functioning of such a cleaning head cannot be ensured. Moreover, it has been observed that such a cleaning head does not give satisfaction, inasmuch as it does not allow effective cleaning of the well to be obtained with certainty.

The present invention therefore aims to correct the disadvantages of the prior art by proposing a new technique for cleaning the wells of a diagnostic test card, designed to completely and reproducibly clean the test sample wells of a diagnostic test card.

To attain such a goal, the object of the invention aims to propose a method for cleaning at least one test sample well, provided in a diagnostic test card, using at least one cleaning head comprising at least one cleaning tube delivering, at its free end, a cleaning fluid, and suction tube mounted within the cleaning tube, for aspirating the contaminated cleaning fluid from its free end located in proximity to the free end of the cleaning tube, the method consisting of providing for relative displacement between the test card and the cleaning head so that the test card occupies a cleaning position wherein the cleaning tube delivers the cleaning fluid, at its free end, into the well to be cleaned, and the suction tube aspirates the contaminated cleaning fluid.

According to the invention, the method consists, in the cleaning position, of providing for intake of air between the exterior and the interior of the free end of the cleaning tube so as to create a vortex in the cleaning fluid within the well to be cleaned.

In addition, the method according to the invention can also exhibit, in combination, at least one and/or another of the following additional features:

providing for relative displacement between the test card and the cleaning head so as to ensure abutment of the free end of the cleaning tube on the test card for the purpose of creating the air intake.

equipping the free end of the cleaning tube so that the free end of the cleaning tube creates the air intake when it is in abutment on the test card, equipping the test card so that said test card creates the air intake when the free end of the cleaning tube is in abutment on the test card, equipping the free end of the cleaning tube with a flexible tip, which either delimits the air intake or ensures fluid-tightness with the card when said tip is in abutment on the test card, ensuring abutment of the free end of the cleaning tube on the card for the purpose of creating a suction zone of predetermined height between the free end of the suction tube and the bottom of the well, creating the suction zone of predetermined height between the free end of the suction tube and the bottom of the well, with the free end of the suction tube extending beyond the free end of the cleaning tube, creating the suction zone of predetermined height between the free end of the suction tube and the bottom of the well, with the free end of the suction tube extending short of the free end of the cleaning tube, aspirating the contaminated cleaning fluid at the free end of the suction tube, at several separate suction sections located, in the cleaning position, vertically above spots placed in the test sample well, providing for relative displacement between the test card and the cleaning head so as to laterally displace the suction zone with a predetermined height between the free end of the suction tube and the bottom of the well when the suction zone does not allow cleaning the bottom of the well in a single position.

Another object of the invention is to propose a cleaning head for at least one test sample well provided in a diagnostic test card, comprising at least one cleaning tube connected to a cleaning fluid source and delivering, at its free end the cleaning fluid, and a suction tube mounted inside the cleaning tube and connected to a suction source and aspirating, at its free end, located in proximity to the free end of the cleaning tube, the contaminated cleaning fluid.

According to the invention, the cleaning tube is provided with an air inlet between the outside and the inside of its free end, in proximity to or on its transverse face.

In addition, the cleaning head according to the invention can also exhibit, in combination, at least one and/or another of the following additional features:

the air intake comprises a series of channels provided on the transverse face delimiting the free end of the cleaning tube, said channels extending radially between the outside wall and the inside wall of the cleaning tube, the channels are distributed evenly over the transverse face of the cleaning tube, the cleaning tube has a rough transverse face delimiting the air intake between the outer wall and the inner wall of the cleaning tube, the free end of the suction tube is located short of the free end of the cleaning tube, the free end of the suction tube is located short of the free end of the cleaning tube by a value comprised between 10 and 300 µm, the cleaning tube is provided with a flexible tip forming the free end of said cleaning tube, the suction tube comprises within it a duct communicating with the suction source and equipped at its free end with partitions delimiting separate suction sections.

Another object of the invention is to propose a cleaning device comprising a cleaning fluid source, a suction source for the contaminated cleaning fluid, at least one cleaning had and a system for relative displacement between the cleaning head and the diagnostic test card wherein is provided at least one test sample well, the displacement system being controlled to occupy at least one well cleaning position.

According to the invention, the device comprises at least one cleaning head, the tube whereof is capable, in the cleaning position, of coming into abutment at its free end on the test card to create an air intake between the outside and the inside of the free end of said cleaning tube.

Various other features are revealed by the description given below with reference to the appended drawings which show, by way of non-limiting examples, embodiments of the object of the invention.

DESCRIPTION OF THE PREFERRED EMBODIMENTS

Figure 1:
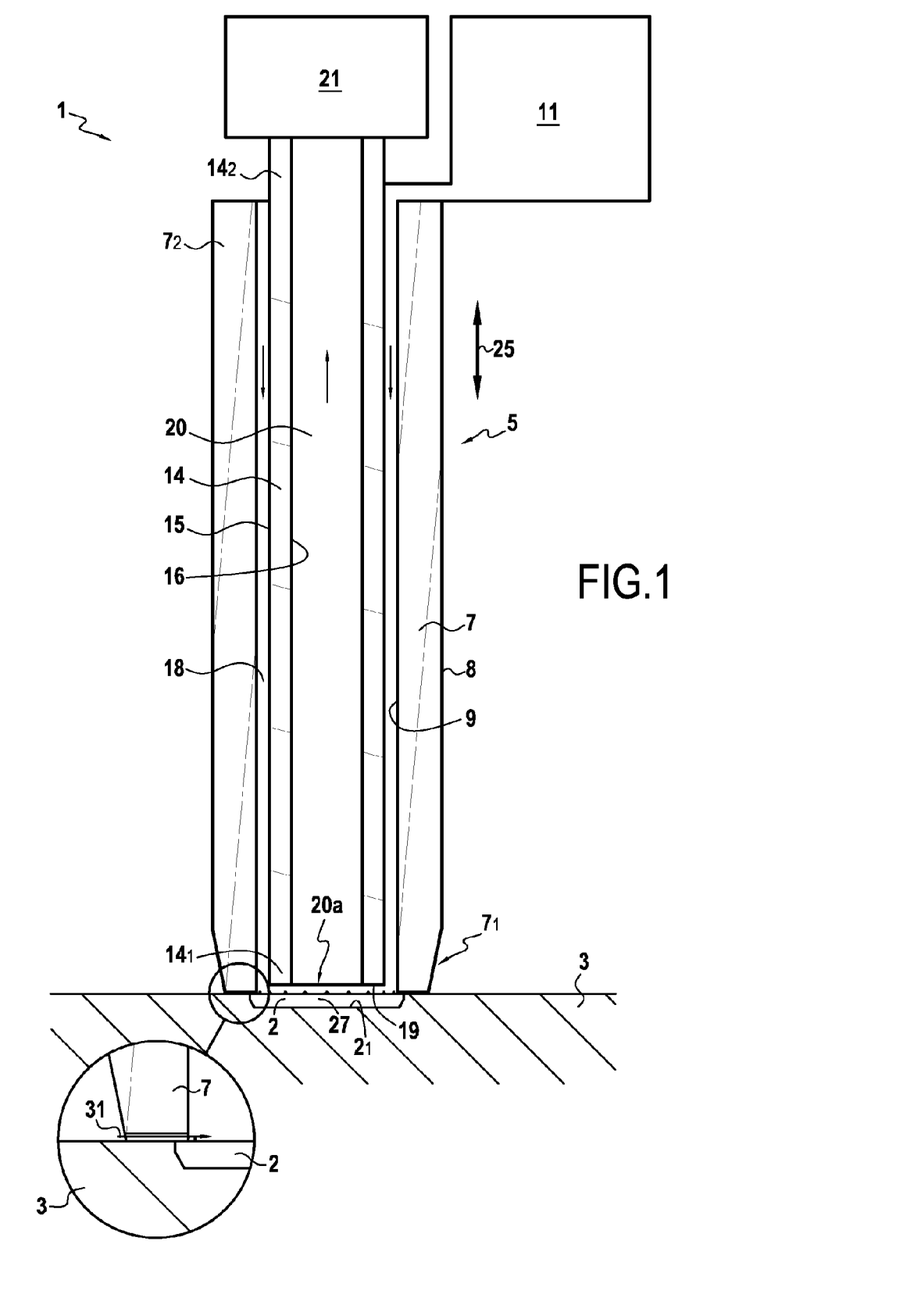
FIG. 1 is an overall view showing a first variant embodiment of a cleaning head conforming to the invention.

La FIG. 1 illustrates by way of an example a cleaning device 1 for at least one test sample well 2 provided in a diagnostic test card 3. The device 1 according to the invention comprises at least one cleaning head 5 capable of cleaning a test sample well 2 in one or more positions depending on the shape of the well, for example in the case of a well with an oblong shape. In the example illustrated in FIG. 1, the device 1 comprises a single cleaning head 5. Of course it is clean that the cleaning device 1 can comprise a plurality of cleaning heads 5 arranged for example side by side in rows and columns, and in distributions identical or not to the test sample wells 2 to be cleaned, provided on the diagnostic test card 3. For example, construction of a cleaning device 1 can be provided for comprising 8 or 12 cleaning heads 5.

Each cleaning head 5 comprises a cleaning tube 7 having for example a circular cross-section. The cleaning tube 7 comprises an outer tubular wall 8 and an inner tubular wall 9. The cleaning tube 7 exhibits a free end $7_1$ delimited by an annular transverse face 10 providing the connection between the outer wall 8 and the inner wall 9. By way of an example, the outer diameter of the cleaning tube 7 is comprised between 0.5 mm and 25 mm and preferably between 0.5 mm and 5 mm.

The free end $7_1$ of the cleaning tube 7 can exhibit different shapes. This, in the example illustrated in FIGS. 1 and 2, the inner wall 9 of the cleaning tube 7 has a constant cross-section over its entire length, while the outer wall 8 of the cleaning 7 has a constant cross-section with the exception of its free end $7_1$ which exhibits a cross-section decreasing up to its transverse face 10. FIG. 3 illustrates another variant embodiment according to which the cross-section of the inner wall 9 of the cleaning tube 7 is constant with the exception of its free end, which decreases up to the transverse face 10.

The cleaning tube 7 exhibits an end $7_2$ opposite to the free end $7_1$ and communicating with a source of cleaning fluid 11. For example, the cleaning fluid used is water with or without added adjuvants, an aqueous and/or organic solvent, a solvent containing proteins, a cleaning buffer which can contained HEPES, sodium chloride, BSA (bovine serum albumin), casein, PEG (polyethylene glycol), sodium nitride, surfactants such as Tween-20, sugar, etc. The cleaning fluid can also include fillers such as talc, particles, corundum, alumina, glass, so as to add mechanical action to the cleaning process.

The cleaning head 5 also comprises a suction tube 14 mounted within the cleaning tube 7 and exhibiting a preferably circular cross-section. For example, the outer diameter of the suction tube 14 is comprised between 0.2 mm and 20 mm and preferably between 0.2 mm and 4 mm. The suction tube 14 comprises an outer tubular wall 15 and an inner tubular wall 16. The suction tube 14 delimits, between its outer wall 15 and the inner wall 9 of the cleaning tube 7, a tubular duct 18 for directing cleaning fluid to the free end $7_1$ of the cleaning tube 7. The suction tube 14 and cleaning tube 7 are preferably mounted coaxially.

The suction tube 14 comprises a free end $14_1$ extending in proximity to the free end $7_1$ of the cleaning tube 7. The free end $14_1$ of the suction tube 14 is delimited by the transverse face 19 connecting between the inner wall 16 and the outer wall 15 of the suction tube 14. The suction tube 14 thus delimits by its inner wall 16 a duct 20 communicating from the end $14_2$ opposite to the free end $14_1$, with a suction source 21 for the contaminated cleaning fluid, aspirated from its free end $14_1$.

By way of an example, the suction source 21 is embodied by a vacuum pump, a venture or the vacuum network. Generally, the flow of the suction source 21 is greater than the flow of the cleaning fluid source 11. The difference between the flows of the cleaning fluid source 11 and the suction source 21 depends in particular on the operating conditions and on the geometry of the cleaning head 5 and of the test sample wells 2 to be cleaned. By way of an example, the ratio of the flow of the suction source to the flow of the cleaning fluid source 11 is comprised between 300 and 3000.

The cleaning device 1 according to the invention also comprises a system 25 for relative displacement between the cleaning head 5 and the diagnostic test card 3 so that the cleaning head 5 occupies at least one first position, called the rest position, wherein the cleaning head is separated from the diagnostic test card 3, and a cleaning position for which the cleaning tube 7 provides delivery of cleaning fluid to the interior of the well and the suction tube 14 aspirates the contaminated cleaning fluid. The displacement system 25, which can be of any inherently known type, is not described more precisely because it is known to those skilled in the art and is not itself a part of the invention.

According to one advantageous embodiment feature, the displacement system 25 is controlled so as to ensure, for the cleaning position, abutment of the cleaning tube 7 on the diagnostic test card 3 at its transverse face 10, while the free end of the suction tube 14 is situated above the bottom $2_1$ of the test sample well 2. In this cleaning position, the cleaning tube partially or totally situated vertically above the test sample well 2. In this cleaning position, the free end, and more precisely the transverse face 19 of the suction tube 14 is situated at a predetermined distance from the bottom of the well to be cleaned 2 so as to delimit, with the latter, a suction zone 27. Advantageously, in the cleaning position, the transverse face 19 of the suction tube 14 is situated at a distance from the bottom of the well to be cleaned 2 which can range from 2 mm for micro-wells and up to 10 mm for micro-plates.

Figure 2:
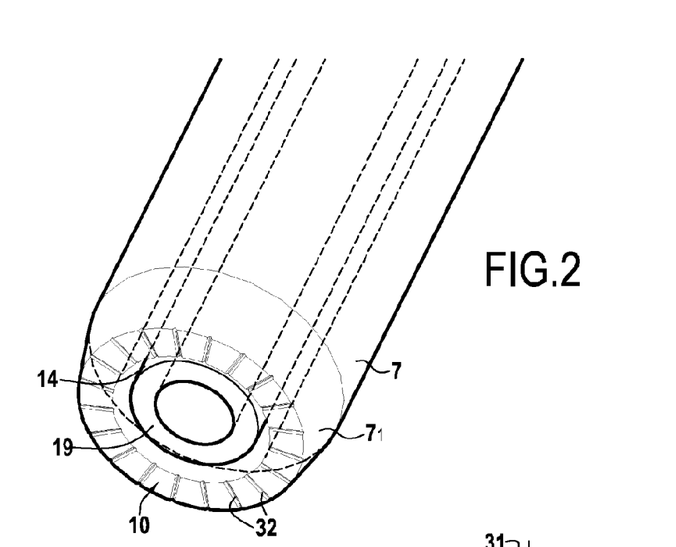
FIG. 2 is a perspective view of the cleaning head illustrated in FIG. 1.
Figure 3:
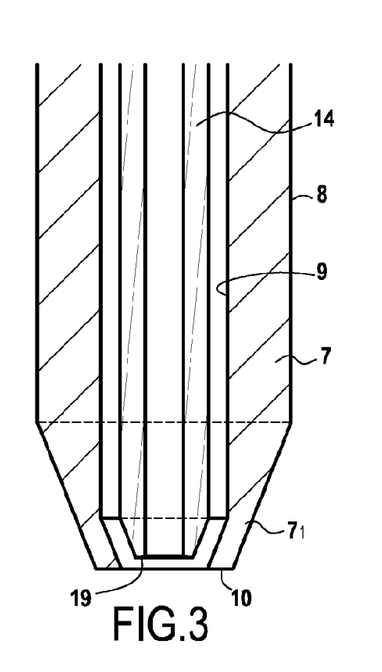
FIG. 3 is a section in elevation showing another embodiment of the variant of the cleaning head illustrated in FIGS. 1 and 2.

According to a preferred embodiment feature illustrated in FIGS. 1 through 3, the free end $14_1$ of the suction tube 14 is set back with respect to the free end $7_1$ of the cleaning tube 7. In other words, the transverse face 19 of the suction tube 14 is set back relative to the transverse face 10 of the cleaning tube 7. According to one advantageous embodiment feature, the transverse face 19 of the suction tube 14 is set back relative to the transverse face 10 of the cleaning tube by a value comprised between 10 μm and 3 mm and preferably, for a micro-plate washing application for example, between 1 mm and 3 mm and again preferably, for a micro-well washing application, between 10 μm and 300 μm.

In conformity with the invention, the cleaning tube 7 is equipped with an air intake 31 between the outer wall 8 and the inner wall 9. In the example illustrated in FIGS. 1 and 2, the air intake 31 comprises a series of channels 32 provided on the transverse face 10 delimiting the free end of the cleaning tube 7. These channels 32 extend radially between the outer wall 8 and the inner wall 9 of the cleaning tube, opening at the outer wall 8 and inner wall 9. The channels 32 lead to or open at the tubular duct 18 for directing the cleaning fluid, which is delimited by the inner wall 9 of the cleaning tube 7. According to a preferred variant embodiment, illustrated more particularly in FIG. 2, the channels 32 are distributed evenly over the transverse face 10 of the cleaning tube 7.

According to another variant embodiment illustrated more particularly in FIG. 3, the cleaning tube 7 has a rough transverse face 10 delimiting the air intake 31 between the outer wall 8 and the inner wall 9 of the cleaning tube 7. According to this variant embodiment, it must be understood that when the transverse face 10 is in abutment on a flat surface, the roughness of the transverse face 10 is such that the latter exhibits protruding portions delimiting between them passages forming together the air intake 31 between the outer wall 8 and the inner wall 9.

According to another variant embodiment, not shown, it is to be noted that the air intake 31 can also be embodied by holes provided radially at the free end $7_1$ of the cleaning tube 7 in proximity to the transverse face 10 and leading to the outer wall 8 and the inner wall 9.

The implementation of the cleaning head 5 follows directly from the foregoing description. The process for cleaning a test sample well 2 thus consists of providing for relative displacement between the cleaning head 5 and the diagnostic test card 3 so as to place the cleaning head 5 in its cleaning position. In this position, illustrated in FIG. 1, the cleaning tube 7 is in abutment at its free end $7_1$ on the test card. In this position, the transverse face 10 of the cleaning tube 7 is in abutment on at least a portion of the perimeter of the test sample well 2. In this position, the cleaning tube 7 is able to inject cleaning fluid inside the well 2 while the suction tube 14 is situated vertically above the well 2 to aspirate the contaminated cleaning fluid. In this position, an air intake 31 appears between the outside and the inside of the cleaning tube 7, through channels 32 for example which allow the air to be directed from the outside of the cleaning tube 7 to the inside of the test sample well 2 to be cleaned.

Injection of the cleaning fluid inside the tube 7 leads to its escape through the free end $7_1$ of the cleaning tube 7. Simultaneously, the suction source 21 aspirates, at the free end $14_1$ of the suction tube 14, the contaminated liquid. As a result of the air intake 31 formed between the outside and the inside of the cleaning tube 7, there occurs within the test sample well 2, a cleaning fluid vortex allowing effective and complete cleaning of the test sample well 2. Inasmuch as the suction tube 14 is situated inside the cleaning tube 7, good recovery of the contaminated cleaning fluid occurs.

It should be noted that the positioning of the free end $14_1$ of the suction tube 14 relative to the free end $7_1$ of the cleaning tube 7 depends in particular on the depth of the test sample well 2 to be cleaned. As indicated above, the free end $14_1$ of the suction tube 14 is advantageously set back relative to the free end $7_1$ of the cleaning tube 7.

Figure 4:
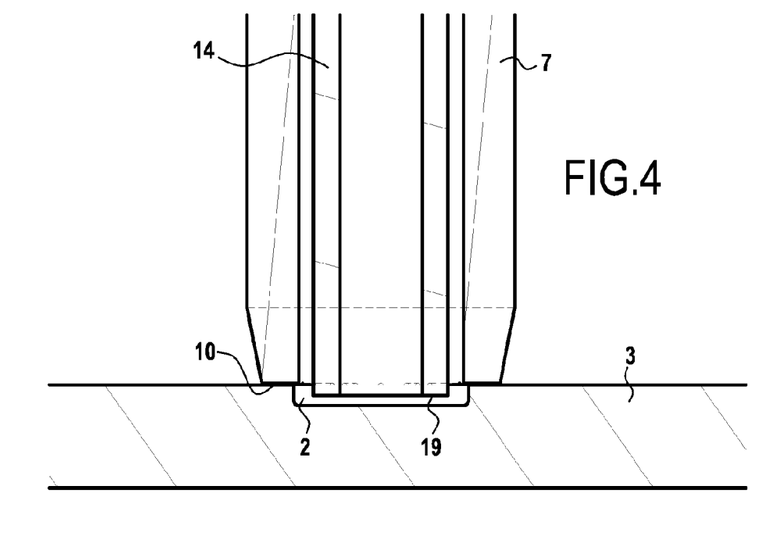
FIG. 4 illustrates another variant embodiment of a cleaning head conforming to the invention.
Figure 5:
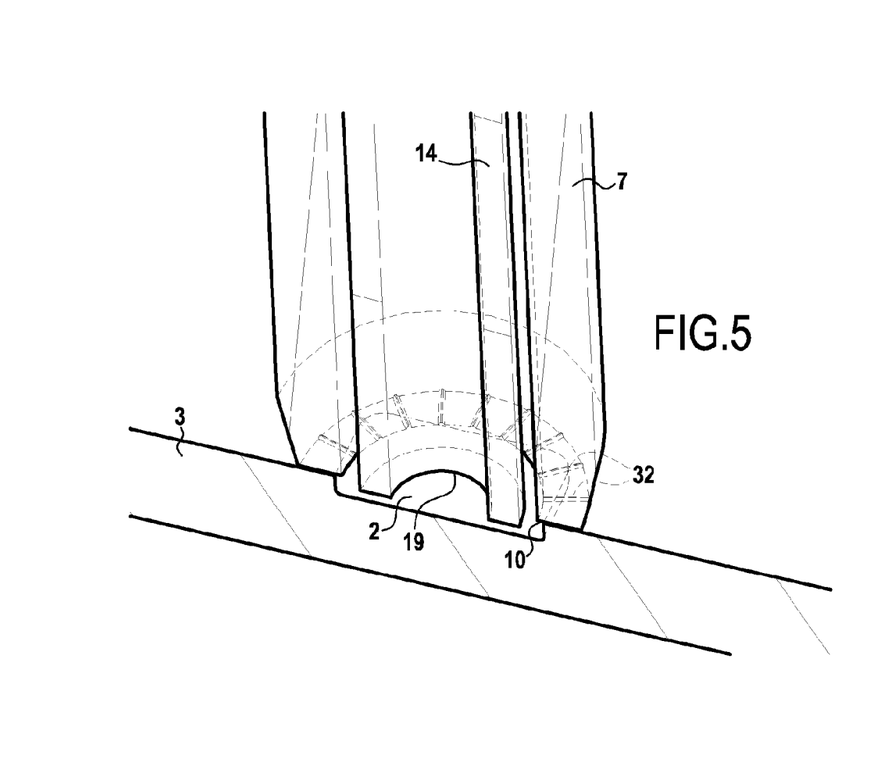
FIG. 5 illustrates a partial cutaway perspective view of the variant embodiment of the cleaning head illustrated in FIG. 4.

Consideration can, however, be given to implementing a cleaning head 5 wherein the free end $14_1$ of the suction tube extends beyond the free end $7_1$ of the cleaning tube 7 as seen more precisely in FIGS. 4 and 5. In other words, the transverse face 19 of the suction tube 14 protrudes with respect to the transverse face 10 of the cleaning tube 7. Such an arrangement can thus be contemplated for test sample wells 2 exhibiting a relatively great depth, allowing the free end $14_1$ of the suction tube 14 to be brought closer to the bottom $2_1$ of the test sample well 2. This variant embodiment makes it possible to maintain a suitable height for the suction zone 27 to ensure good aspiration of the contaminated cleaning fluid. Advantageously, as previously stated, in the cleaning position the transverse face 19 of the suction tube 14 is situated at a distance from the bottom of the well to be cleaned 2 which can range from 2 mm for micro-wells up to 10 mm for micro-plates.

In the foregoing examples, the air intake 31 between the outside and the inside of the free end $7_1$ of the cleaning tube 7 is implemented by the geometry of the cleaning tube 7.

Figure 6:
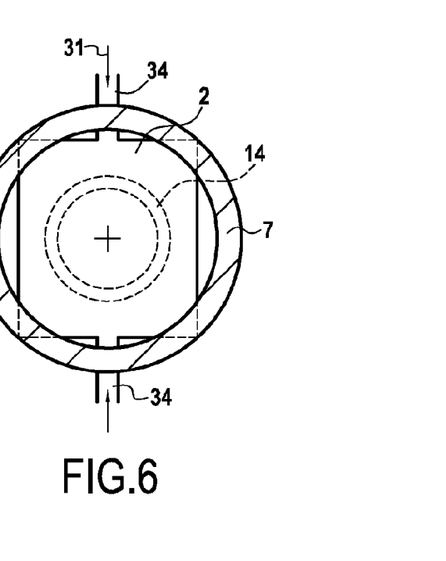
FIG. 6 is a sectional view of another variant embodiment of the cleaning head conforming to the invention.

FIG. 6 illustrates another exemplary embodiment wherein the air intake 31 is implemented by the geometry of the diagnostic test card 3. According to this exemplary embodiment, the test sample well 2 communicates with at least one and, in the example illustrated in FIG. 6, two ducts 34 provided in the diagnostic test card 3 and forming the air intake 31. These ducts 34 are provided such that in the position of the free end $7_1$ of the cleaning tube 7 abutting on the diagnostic test card 3, the ducts 34 extend to either side of the inner 9 and outer 8 walls to allow entry of air into the cleaning tube 7. In this abutment position, the cleaning tube 7 surrounds or completely closes off the well 2, with the exception of the ducts 34. The cleaning tube 7 provides a seal between the cleaning head 5 and the diagnostic test card 3.

According to one exemplary embodiment, the free end $7_1$ of the cleaning tube 7 is designed to provide a seal with the diagnostic test card 3. According to one variant embodiment, the cleaning tube 7 is provided, at its free end $7_1$, with a flexible tip providing a seal with the test card. Such a flexible tip also makes it possible to achieve soft contact between the cleaning tube 7 and the diagnostic test card 3, and to compensate for tolerances in the displacement system 25 to provide for positioning the cleaning head 5 in its cleaning position.

Such a flexible tip can be added to the free end $7_1$ of the cleaning tube, or be overmolded or co-injected at the free end $7_1$ of the cleaning tube 7. For example, the flexible tip can exhibit a Shore A hardness comprised between 20 and 80. Such a tip can be made of silicone, of elastomers such as EPDMs (Ethylene Propylene Diene Monomer), SBR (Styrene Butadiene Rubber) . . . or others, or of thermoplastic elastomers such as Arnitel, Pebax . . . or others.

Of course, consideration can also be given to having such a flexible tip able to also delimit the air intake 31 for example, by comprising channels 32.

Figure 7:
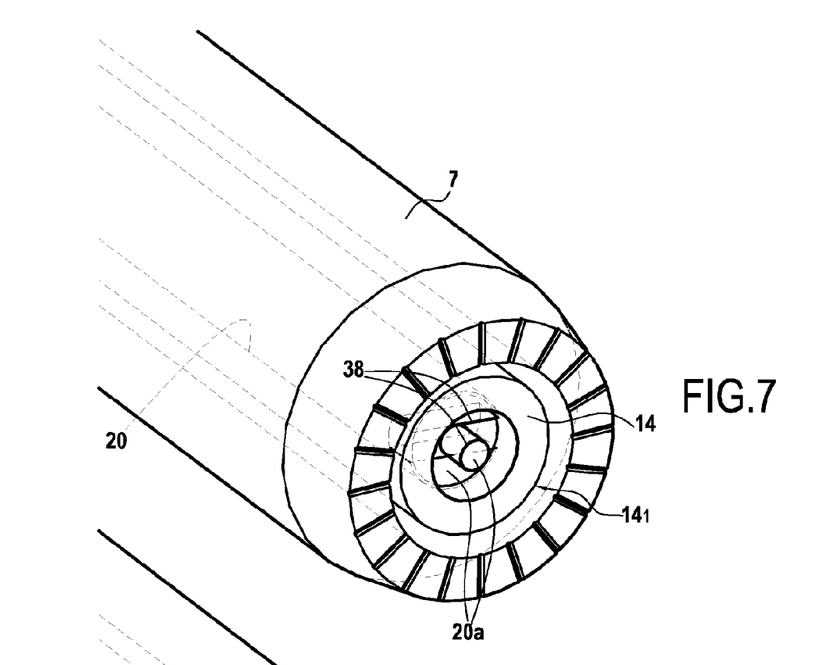
FIG. 7 illustrates a variant embodiment of the suction tube forming part of a cleaning head conforming to the invention.
Figure 8:
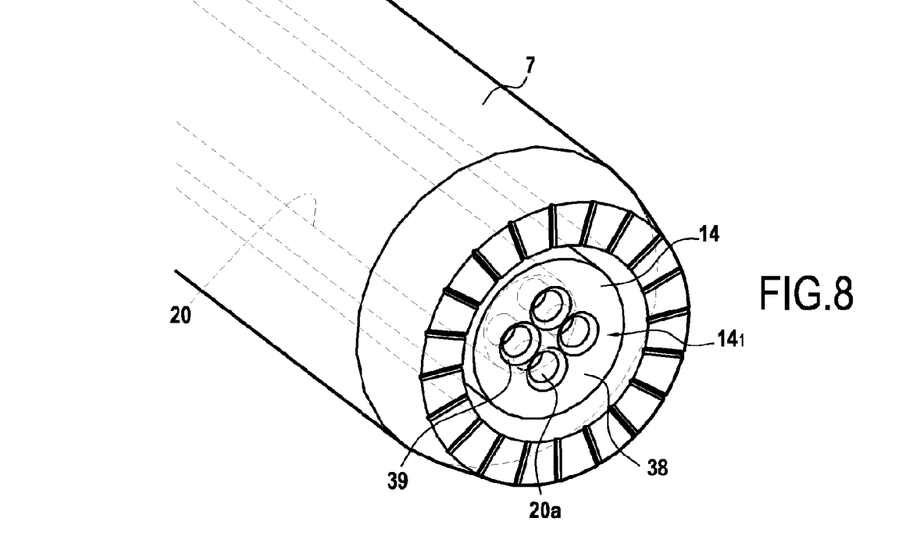
FIG. 8 illustrates another variant embodiment of the suction tube forming part of a cleaning head conforming to the invention.

In the foregoing examples, the suction tube 14 comprises within it a duct 20 opening at the free end $14_1$, with a single suction section 20a, corresponding to the full cross-section of the duct 20. FIGS. 7 and 8 illustrate another variant embodiment of the suction tube 14 allowing aspiration of the contaminated cleaning fluid at the free end $14_1$, at several suction sections 20a separated from one another by partitions 38. These suction sections 20a are provided at the free end $14_1$ of the suction tube 14 such that, in the cleaning position, these suction sections 20a are located vertically above spots placed in the test sample well 2. Such an arrangement contributes toward reinforcing the cleaning of the well 2 and more particularly in the deposit areas of one or more products of interest, called spots.

In the example illustrated in FIG. 7, the duct 20 of the suction tube 14 is equipped at the free end $14_1$ of the suction tube 14, with partitions 38 which are arranged in any appropriate manner for forming a specific geometry or pattern. These partitions 38 delimit suction sections 20a which, in the example illustrated in FIG. 7 have different shapes. FIG. 8 illustrates another variant embodiment wherein the suction tube 14 comprises suction sections 20a having identical shapes, to with circular for example. According to this variant embodiment, the duct 20 of the suction tube 14 opens at the free end $14_1$, for example at four suction sections 20a separated from one another by partitions 38 made on a transverse face closing off the free end $14_1$ of the suction tube 14.

In the example illustrated in FIG. 8, each suction section 20a is equipped with a conical entry 39 converging toward the duct 20 of the suction tube 14 to facilitate the selective routing of the contaminated cleaning fluid through the suction sections 20a. Of course, it can be provided that the suction sections 20a of the example illustrated in FIG. 8, are made without the conical entries 39.

In the foregoing examples, a relative displacement is carried out between the cleaning head 5 and the diagnostic test card 3 so as to place the cleaning head 5 in a cleaning position. It should be noted that provision can also be made for providing the relative displacement between the test card and the cleaning head so as to laterally displace the suction zone at a predetermined height between the free end of the suction tube and the bottom of the well when the suction zone does not allow cleaning the bottom of the well in a single cleaning position.

The invention is not limited to the examples described and shown, because various modifications can be applied to it without departing from its scope.

The invention claimed is:

1. A method for cleaning at least one test sample well, provided in a diagnostic test card, using at least one cleaning head comprising at least one cleaning tube delivering, at its free end, a cleaning fluid, and a suction tube mounted within the cleaning tube for aspirating a contaminated cleaning fluid from its free end located in proximity to the free end of the cleaning tube, the method comprising:
    providing a relative displacement between the test card and the cleaning head, so that the test card occupies a cleaning position wherein the cleaning tube delivers, at its free end, the cleaning fluid inside the sample well to be cleaned and the suction tube aspirates the contaminated cleaning fluid,
    in the cleaning position, abutting the free end of the cleaning tube on the test card,
    delivering the cleaning fluid from the free end of the cleaning tube along a delivery direction, in a direction of a transverse bottom wall of the sample well, and simultaneously aspirating the contaminated cleaning fluid with the aspiration tube,
    thereby allowing an air intake between the outside and the inside of the free end of the cleaning tube, along a direction perpendicular to the delivery direction, thus creating a cleaning fluid vortex within the sample well when the contaminated cleaning fluid is aspirated.

2. The method according to claim 1, wherein the free end of the cleaning tube is provided with a flexible tip which either delimits the air intake, or provides a seal with the test card when said tip is in abutment on the test card.

3. The method according to claim 1, wherein the suction tube comprises a plurality of separate suction sections at its free end.

4. The method according to claim 1, wherein the free end of the cleaning tube has a transverse surface, and wherein abutting the free end of the cleaning tube on the test card, allows an air intake proximate to, or on, the transverse surface of the cleaning tube.

5. The method according to claim 1, wherein the relative displacement between the test card and the cleaning head is provided to create the air intake.

6. The method according to claim 5, comprising configuring the test card so that said test card creates the air intake when the free end of the cleaning tube is in abutment on the test card.

7. The method according to claim 1, wherein abutting the free end of the cleaning tube on the test card creates a suction zone with a predetermined height between the free end of the suction tube and the bottom of the sample well.

8. The method according to claim 7, comprising creating the suction zone with the predetermined height between the free end of the suction tube and the bottom of the well, wherein the free end of the suction tube protrudes with respect to the free end of the cleaning tube.

9. The method according to claim 7, comprising creating the suction zone with the predetermined height between the free end of the suction tube and the bottom of the sample well, wherein a height difference exists between the free end of the cleaning tube and the free end of the suction tube with respect to the bottom of the sample well.

\* \* \* \* \*